(12) United States Patent  (10) Patent No.: US 8,715,705 B2
Maguire et al.  (45) Date of Patent: May 6, 2014

(54) MULTILAYER MEDICAL DEVICES HAVING AN ENCAPSULATED EDGE AND METHODS THEREOF

(75) Inventors: Seamus Maguire, Athlone (IE); Paul Waldron, Galway (IE); Roger Harrington, Athlone (IE); Theodore H. Moore, El Paso, TX (US)

(73) Assignee: Covidien LP, Mansfield, MA (US)

( * ) Notice: Subject to any disclaimer, the term of this patent is extended or adjusted under 35 U.S.C. 154(b) by 1186 days.

(21) Appl. No.: 12/511,282

(22) Filed: Jul. 29, 2009

(65) Prior Publication Data

US 2011/0027334 A1  Feb. 3, 2011

(51) Int. Cl.
*A61F 13/00* (2006.01)

(52) U.S. Cl.
USPC .......................................................... 424/422

(58) Field of Classification Search
USPC .......................................................... 424/423
See application file for complete search history.

(56) References Cited

U.S. PATENT DOCUMENTS

| | | | |
|---|---|---|---|
| 2,862,498 A | 12/1958 | Weekes | |
| 3,416,531 A | 12/1968 | Edwards | |
| 3,498,286 A | 3/1970 | Polanyi et al. | |
| 3,508,554 A | 4/1970 | Sheridan | |
| 3,528,869 A | 9/1970 | Dereniuk | |
| 3,561,493 A | 2/1971 | Maillard | |
| 3,695,921 A | 10/1972 | Shepherd et al. | |
| 3,788,326 A | 1/1974 | Jacobs | |
| 3,862,635 A | 1/1975 | Harautuneian | |
| 3,865,666 A | 2/1975 | Shoney | |
| 3,880,168 A | 4/1975 | Berman | |
| 3,959,429 A | 5/1976 | Benning | |
| 4,225,371 A | 9/1980 | Taylor et al. | |
| 4,284,459 A | 8/1981 | Patel et al. | |
| 4,504,268 A | 3/1985 | Herlitze | |
| 4,782,834 A | 11/1988 | Maguire et al. | |
| 4,791,923 A * | 12/1988 | Shapiro | 128/207.15 |
| 5,540,224 A | 7/1996 | Buret et al. | |
| 5,618,567 A | 4/1997 | Hara et al. | |
| 5,770,134 A | 6/1998 | Hara et al. | |
| 6,022,602 A | 2/2000 | Nomura | |
| 6,055,984 A | 5/2000 | Brain | |
| 6,165,166 A | 12/2000 | Samuelson et al. | |
| 6,464,683 B1 | 10/2002 | Samuelson et al. | |
| 6,698,428 B2 | 3/2004 | Brain | |
| 7,175,734 B2 | 2/2007 | Stewart et al. | |
| 2004/0220534 A1 | 11/2004 | Martens et al. | |
| 2005/0220835 A1 * | 10/2005 | Jayaraman et al. | 424/423 |
| 2006/0118121 A1 | 6/2006 | Martens et al. | |
| 2006/0118122 A1 | 6/2006 | Martens et al. | |
| 2006/0161100 A1 | 7/2006 | Hamboly | |
| 2006/0207602 A1 | 9/2006 | Kolobow et al. | |

(Continued)

OTHER PUBLICATIONS

Guevara et al ("Bacterial adhesion to cerebrospinal fluid shunts", Journal of Neurosurgery, 1987, vol. 67, No. 3, pp. 438-445).*

(Continued)

*Primary Examiner* — Benjamin Packard

(57) ABSTRACT

The present disclosure describes a medical which includes a body defining a conduit. The body includes a multilayer wall having at least one edge. The wall including a core layer positioned between an inner layer and an outer layer, wherein at least one of the inner and outer layers encapsulates the core layer along the edge.

27 Claims, 8 Drawing Sheets

(56) References Cited

U.S. PATENT DOCUMENTS

| | | | |
|---|---|---|---|
| 2007/0218298 A1* | 9/2007 | Terry | 428/447 |
| 2007/0276486 A1* | 11/2007 | Marten et al. | 623/9 |
| 2008/0078406 A1 | 4/2008 | Clayton et al. | |
| 2008/0086214 A1* | 4/2008 | Hardin et al. | 623/23.7 |
| 2008/0193583 A1 | 8/2008 | Kikusawa | |

OTHER PUBLICATIONS

Shah (Published on MDDI Medical Device and Diagnostic Industry News Products and Suppliers, Sep. 2002).*

* cited by examiner

MULTILAYER MEDICAL DEVICES HAVING AN ENCAPSULATED EDGE AND METHODS THEREOF

BACKGROUND

1. Technical Field

The present disclosure relates to medical devices, and more particularly relates to tubular medical devices including a multilayer wall having an encapsulated edge.

2. Background of Related Art

In the course of treating a patient, a tube or other medical device may be used to control the flow of air, food, fluids, or other substances into and/or out of the patient. For example, medical devices, such as tracheal tubes, may be used to control the flow of one or more substances into or out of a patient. In many instances, the device may be left in the patient for periods of time sufficient for microbial growth to occur on the device.

Microbial growth on the device may create the formation of a biofilm on the inside or outside of the tube. Microbial growth on the device may also increase the amount of mucus build up on the tube increasing the resistance to the flow of air through the tube. In addition, the formation of a biofilm is generally not desirable, as biofilms may be related to certain clinical complications, such as Ventilator-Assisted Pneumonia (VAP).

Various techniques have been employed to prevent the build up of microbes on the device. These include coating hydrophobic materials with hydrophilic materials and/or antimicrobial materials, such as silver. Although such techniques have been proven effective in slowing the growth of microbes on the surface of the device, many devices still include areas which remain susceptible to microbial growth. For instance, many devices are formed prior to being machined into a final shape, size or dimension. Thus, the device may be drilled, punched or cut after the device has been coated. Drilling, punching or cutting the device creates an edge along a portion of the exterior of the device wherein the hydrophobic materials are no longer coated with the hydrophilic material. The re-exposure of the hydrophobic material creates areas along the edge of the device which promote microbial growth.

Therefore it would be desirable to provide a device which does not include an edge susceptible to microbial growth.

SUMMARY

Medical devices are described herein which include a body defining a conduit, wherein the body contains a multilayer wall having an outer edge along at least one of a proximal end and a distal end. The multilayer wall has a core layer positioned between an inner layer and an outer layer. In embodiments, at least one of the inner and outer layers encapsulates the core layer along the outer edge on at least one of the proximal and distal ends of the multilayer wall.

In embodiments, the device further includes a hole defined by an inner edge in the multilayer wall. At least one of the inner and outer layers encapsulates the core layer along the inner edge of the hole defined within the wall.

Methods of forming such medical devices are also described. For instance, methods of encapsulating a core layer of a multilayer wall of a medical device include providing a medical device having a body defining a conduit, the body including a multilayer wall having an outer edge along at least one of a proximal end and a distal end. The multilayer wall has a core layer positioned between an inner layer and an outer layer. In embodiments, a mold is positioned on at least one of the proximal and distal ends of the wall creating a cavity between the mold and the end of the wall. At least one of the inner and outer layers positioned within the mold is softened to flow into the cavity and form an encapsulating layer over the core layer. The encapsulating layer is allowed to harden thereby encapsulating the core layer along the outer edge on at least one of the proximal and distal end.

In embodiments, a mold is positioned within a hole defined within the multilayer wall by an inner edge. A cavity is created between the mold and the inner edge of the hole in the wall. At least one of the inner and outer layers positioned within the mold is softened to flow into the cavity and form an encapsulating layer over the core layer. The encapsulating layer is allowed to harden thereby encapsulating the core layer along an inner edge of the hole defined within the wall of the device.

BRIEF DESCRIPTION OF THE DRAWINGS

Various embodiments of the present disclosure will be discussed in more detail below in conjunction with selected embodiments and the appended drawings wherein.

DETAILED DESCRIPTION

Figure 1A:
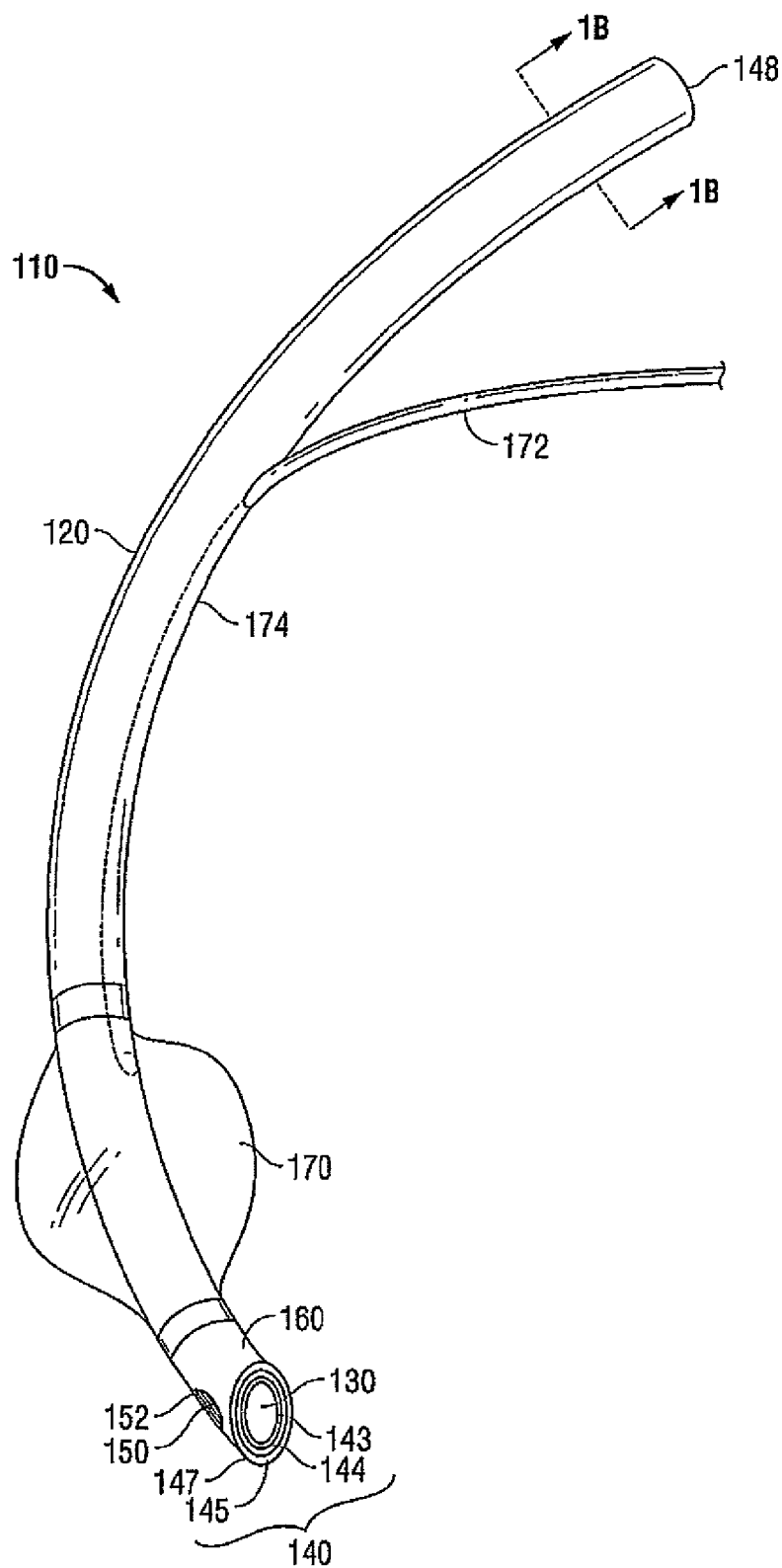
FIG. 1A shows a perspective view of a medical device known in the prior art.

The present disclosure describes a wide variety of medical devices. Medical devices are devices which may be used around or inserted into a living body of any animal. In embodiments, the medical device is a tracheal tube. Although a tracheal tube is used as an example in the figures, the present disclosure is not meant to be limited to tracheal tubes. Some additional non-limiting examples of useful medical devices include: nasal cannulae; stents; tubes, such as administration tubes, duodenal tubes, rectal tubes, drainage tubes, feeding tubes, breathing tubes, and intravenous tubes; catheters, such as suction catheters, delivery catheters, and the like; stents, breathing circuits, and related airway accessories such as connectors, and adapters as well.

The medical device includes a body defining a conduit formed therethrough. The body includes a wall having a plurality of layers. The multilayer wall may consist of any number of layers. In embodiments, the multilayer wall may include at least three layers. In embodiments, the multilayer wall may include an inner layer, an outer layer and core layer positioned therebetween.

The core layer of the wall may be made from any biocompatible polymeric material. In embodiments, the core layer is made from a biocompatible hydrophobic material. Some useful non-limiting examples of hydrophobic materials include polypropylene, polyethylene, hydrophobic polyurethanes, silicones, silicon rubbers, siloxanes, polydimethylsiloxanes, polyvinyl chloride and combinations thereof. In embodiments, the core layer is made from poly vinyl chloride.

The inner and outer layers also may be made from any biocompatible polymeric material. In addition, the inner and outer layers may be the same or different biocompatible materials. In embodiments, the inner and outer layers may be made from a biocompatible hydrophilic material. Some useful non-limiting examples of hydrophilic materials include hydrophilic polyurethanes, sodium, potassium and calcium alginates, carboxymethylcellulose, agar, gelatin, polyvinyl alcohol, collagen, pectin, chitin, chitosan, poly (α-amino acids), polyester, poly-1-caprolactone, polyvinylpyrrolidone, polyethylene oxide, polyether, polysaccharide, polyhydroxyacrylate, polymethacrylate, dextran, xanthan, hydroxypropyl cellulose, methyl cellulose, bioabsorbable glasses, acrylates and methacrylates having hydrophilic esterifying groups, hydroxyacrylate, and acrylic acid, and combinations thereof. In embodiments, the inner and outer layers may include a hydrophilic polyurethane.

The biocompatible materials used to form the multilayer wall may be further combined with at least one bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes.

Examples of classes of bioactive agents which may be utilized in accordance with the present disclosure include anti-adhesives, antimicrobials, analgesics, antipyreties, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Anti-adhesive agents can be used to prevent adhesions from forming between the implantable medical device and the surrounding tissues opposite the target tissue. In addition, anti-adhesive agents may be used to prevent adhesions from forming between the coated implantable medical device and the packaging material. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents which may be included as a bioactive agent in the bioactive coating of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the bioactive coating of the present disclosure.

Also a number of inorganic materials have been shown to possess antimicrobial activity. They include metal ions such as silver, copper, zinc, mercury, tin, lead, bismuth, cadmium, chromium and thallium ions. It is theorized that these antimicrobial metal ions exert their effects by disrupting respiration and electron transport systems upon absorption into bacterial or fungal cells. Antimicrobial metal ions of silver, copper, zinc, and gold, in particular, are considered safe for in vivo use. Antimicrobial silver ions are particularly useful for in vivo uses due to the fact that they have the highest ratio of efficacy to toxicity.

In embodiments, antimicrobial agent may be elemental silver or silver compounds, such as silver oxide, silver chloride, silver nitrate, silver sulfadiazine, silver sulfate, silver bromide, silver iodide and the like. Elemental silver and/or silver compounds may also be combined with other hydrophilic materials, such as bioabsorbable glass and/or hydrophilic polyurethanes, to form a compound which possess antimicrobial activity on or near the surface of a medical device.

Other bioactive agents which may be included as a bioactive agent in the coating composition applied in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents which may be included in the coating composition include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; and ribozymes.

The biocompatible materials used to form the inner and outer layers may possess a lower melting temperature than the biocompatible material used to form the core layer of the wall. In embodiments, the difference between the melting temperatures of the core layer and the inner and outer layers is at least about 10° C. In embodiments, the difference between the melting temperatures of the core layer and the inner and outer layers is at least about 20° C. In one example, a hydrophilic polyurethane having a melting temperature of about 180° C. may form the inner and/or outer layers on a core layer formed of polyvinyl chloride having a melting temperature of about 190° C. Because the melting temperature of the polyurethane is less than that of the polyvinyl chloride, the inner and outer layers of the wall can be exposed to a temperature near, at or even slightly above the melting point of the hydrophilic polyurethane to soften the inner and outer layers with out softening the core layer.

In embodiments, the biocompatible materials used to form the inner and outer layers may possess a lower melt flow viscosity than the biocompatible material used to form the core layer of the wall. In embodiments, the difference between the melt flow viscosity of the core layer and the inner and outer layers is at least about 5 g/10 min at a temperature of 120° C. In embodiments, the difference between the melt flow viscosity of the core layer and the inner and outer layers is at least about 10 g/10 min at a temperature of 120° C. In one example, a hydrophilic material such as polyvinyl pyrrolidone having a melt flow viscosity of about 20 g/10 min at a temperature of 120° C. may form the inner and outer layers on a core layer formed of a silicone material having a melt flow viscosity of about 15 g/10 min at a temperature of 120° C. Because the melt flow viscosity of the polyvinyl pyrrolidone is less than that of the silicone material, the inner and outer layers may flow easier when softened than the silicone material.

Prior to the encapsulation of the core layer along an edge of the device, the body of the device may be formed using any suitable methods known to those skilled in the art for forming multilayer tubular medical devices. Some non-limiting examples include extrusion processes, such as cold extrusion, hot extrusion, warm extrusion, and co-extrusion processes, as well as molding processes such as, injection molding, compression molding, blow molding, rotational molding and co-molding processes and combinations thereof. Some specific examples of suitable processes are also described in U.S. Published Patent Application Nos.: 2004/0220534; 2006/0118121; and 2006/0118122, the entire contents of each of which is incorporated herein by reference.

In some embodiments, the layers of the wall of the medical device may formed simultaneously through the process of co-extrusion. For example, a biocompatible hydrophobic material, such as polyvinyl chloride, may be co-extruded between two layers of a biocompatible hydrophilic material, such as polyurethane combined with a silver bioactive agent and/or a bioabsorbable glass, to form a multilayer wall defining a conduit.

In other embodiments, the core layer may be formed separate from the inner and outer layers. For example, the core layer may be extruded or molded to form a conduit therethrough. The inner and outer layers may then be applied to the core layer as a coating. The inner and outer layers may be applied to the core layer using any suitable coating method known to those skilled in the art including, dip-coating, wiping, brushing, spraying, rolling and combinations thereof.

The medical devices described herein include at least one edge. An outer edge may be positioned along the proximal and/or distal end of the device. An inner edge may be positioned along a hole defined within the wall of the device. In embodiments, the at least one edge may be created after the inner and outer layers are positioned on the core layer.

The medical devices described herein may include at least one hole. The hole is defined by an inner edge in the multilayer wall and connects the conduit to the outer surface of the body of the device. Prior to encapsulation, the core layer and the inner and outer layers are exposed along the inner edge. It is envisioned that the hole may be of any size shape or dimension.

The hole may be formed using any suitable method. For example, the hole may be formed during a molding or extruding process during the manufacturing of the complete device. Another example includes drilling, slicing or punching the hole out of the wall after the device is formed. In some embodiments, the hole may be a Murphy's eye, which is an opening in the tube which may be positioned near the distal end of the tracheal tube and is often positioned opposite the beveled edge of the tube. The purpose of a Murphy's eye is to provide an alternate pathway for fluid to flow if the bevel edge of the tube is occluded. Of course the Murphy's eye may be positioned anywhere along the tube.

Figure 1B:
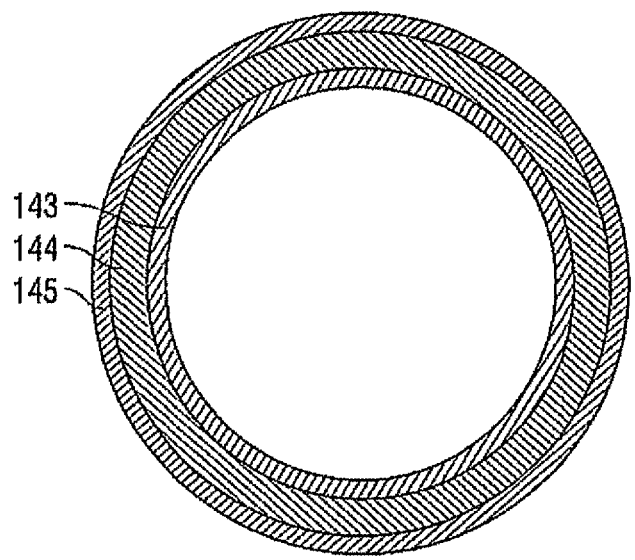
FIG. 1B shows a cross-sectional view of the prior art medical device of FIG. 1A.

In embodiments, the hole may be an evacuation port, which is opening in the tube which is often positioned on the tube proximal to a cuff. The cuff is used to anchor the device into place and by doing so creates a space on the outside of the tube and proximal to the cuff for mucous build-up and/or microbial growth to occur. An evacuation port which is positioned proximal to the cuff permits access to the created space and allows for the removal of mucous build-up and/or microbial growth Turning now to FIGS. 1A and 1B, a prior art tubular medical device 110 is shown including body 120 defining conduit 130 therethrough. Body 120 includes multilayer wall 140 which includes core layer 144 positioned between inner layer 143 and outer layer 145. First outer edge 147 is located on the proximal end of wall 140. Second outer edge 148 is located on distal end of wall 140. Device 110 also includes inflatable cuff 170 connected to inflatable hose 172 via inflation lumen 174. Wall 140 further includes hole 150 defined by inner edge 152 which connects conduit 130 to outer surface 160 of device 110. Inner layer 143 and outer layer 145 cover core layer 144 along the entire longitudinal length of wall 140, however core layer 144 is exposed along first outer edge 147 and second outer edge 148 of wall 140. In addition core layer 144 is exposed along inner edge 152 of hole 150. The prior art devices as shown in FIGS. 1A and 1B continue to expose the hydrophobic portions of the device, i.e., core layer 144, to the surrounding tissue making the device susceptible to microbial growth in the exposed areas.

Figure 2A:
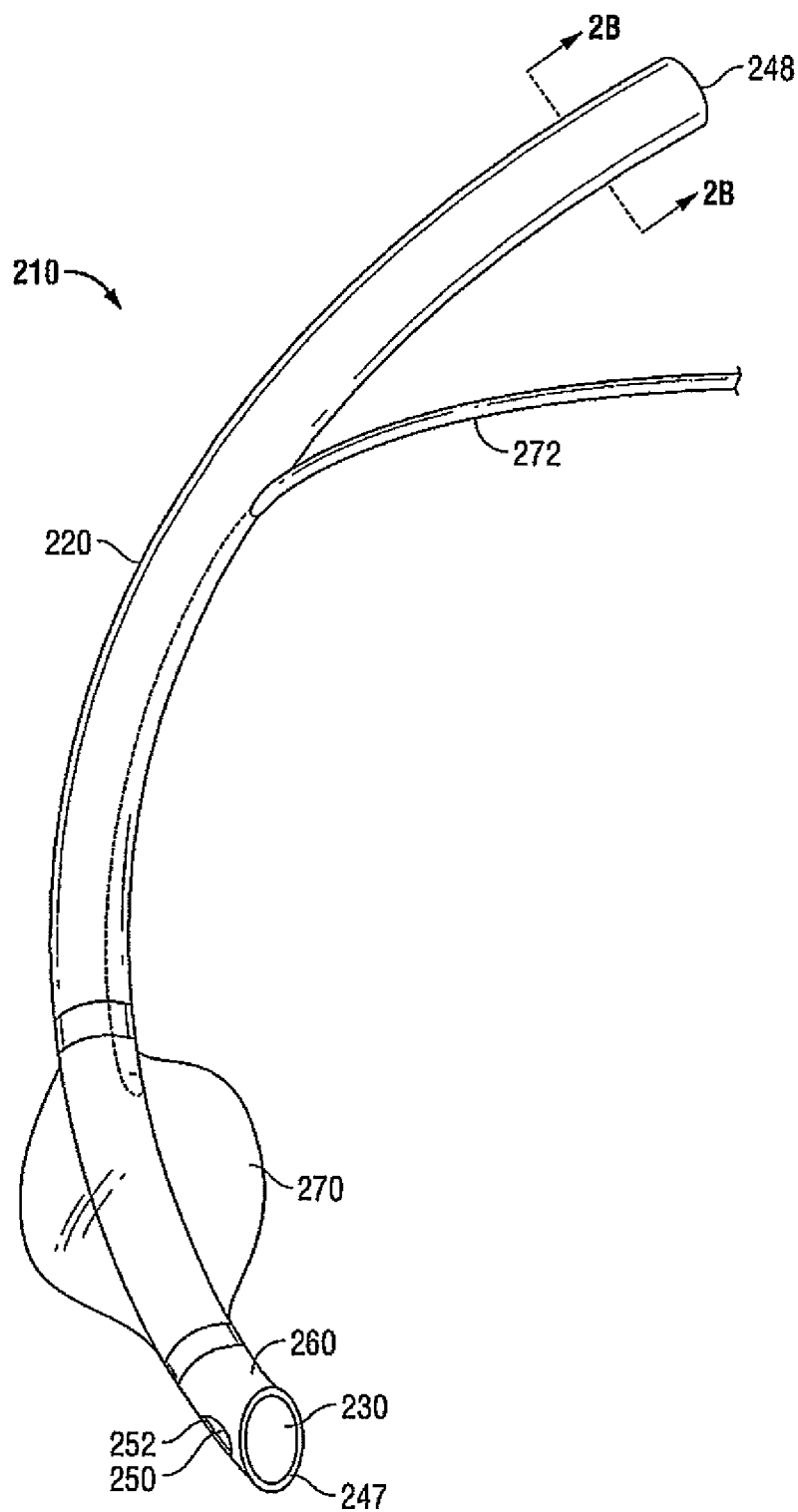
FIG. 2A shows a perspective view of one embodiment of a medical device according to the present disclosure.
Figure 2B:
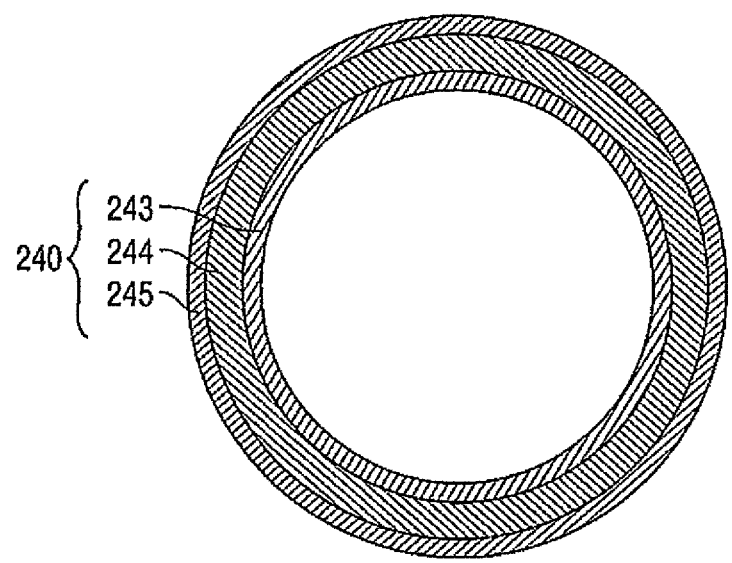
FIG. 2B shows a cross-sectional view of the device of FIG. 2A as described in at least one of the embodiments in the present disclosure.

As depicted in FIGS. 2A and 2B, medical device 210 includes body 220 defining conduit 230 therethrough. Body 220 includes multilayer wall 240 which includes core layer 244 positioned between inner layer 243 and outer layer 245. First outer edge 247 is located on the proximal end of wall 240 and second outer edge 248 is located on the distal end of wall 240. Wall 240 further includes hole 250 defined by inner edge 252 which connects conduit 230 to outer surface 260 of device 210. Inner layer 243 and outer layer 245 cover core layer 244 along the entire longitudinal length of wall 240. Core layer 244 is also covered by at least one of inner layer 243 and outer layer 245 along first outer edge 247, second outer edge 248 of wall 240 and inner edge 252. Although the inner and outer layers are shown to encapsulate all the edges of the medical device wherein the core layer may have been exposed, it is envisioned that the inner and outer layers may only encapsulate the core layer along only one edge and/or any combination of edges of the medical device.

The core layer may be encapsulated by the layers along the inner and/or outer edges of the devices described herein using a variety of methods. In embodiments, a mold is positioned along at least one of the proximal and distal ends of the wall. The mold is configured to interact with the inner and outer layers along the outer edges of the device. In embodiments, the mold is in physical contact with both the inner and outer layers. In embodiments, the mold may be capable of applying direct pressure to the inner and/or outer layers. The mold is also configured to not interact with the core layer. In fact, when the mold is properly positioned along an outer edge, an air gap is created between the core layer and the mold. The air gap provides a cavity for the inner and/or outer layers to flow into when softened.

In embodiments, a mold may be positioned along an inner edge of the wall. The inner edge defines a hole in the multilayer wall which connects the conduit to the outer surface of the device. The mold is configured to interact with the inner and outer layers along the inner edge. However, the mold is configured to be slightly smaller than the hole defined by the inner edge. The difference in size between the hole and the mold allows the mold to enter the hole without interacting with the core layer directly and also creates an air gap between the mold and the core layer inside the hole. The air gap provides a cavity for the inner and/or outer layers to flow into when softened.

The mold may be connected to a power source to provide energy to the mold to soften the inner and outer layers. The mold may be energized using any method suitable for softening the layers to at least a flowable state. For instance, the mold may heat the layers using ultrasonic energy, RF energy, electrical energy, solar energy, and the like. By flowable state, the inner and outer layers may be softened to the point in which a combination of the energy and pressure may be applied to the layers from the mold to allow the layers to move into the cavity created by the mold and encapsulate the core layer.

In embodiments, the mold may be a stationary mold in which the outer and/or inner edges of the medical device are pressed into the mold to create the encapsulated edge. In embodiments, the mold may be a hand-held tool used to encapsulate the outer and/or inner edges of the wall. The mold may be formed as a one-piece or multi-piece device. In embodiments, the mold is a two-part tool capable of being pressed together when contacting the outer and/or inner edges of the wall. By pressing the two-part tool together, varying amounts of pressure may be applied to the inner and outer layers along an edge of the device.

Figure 3A:
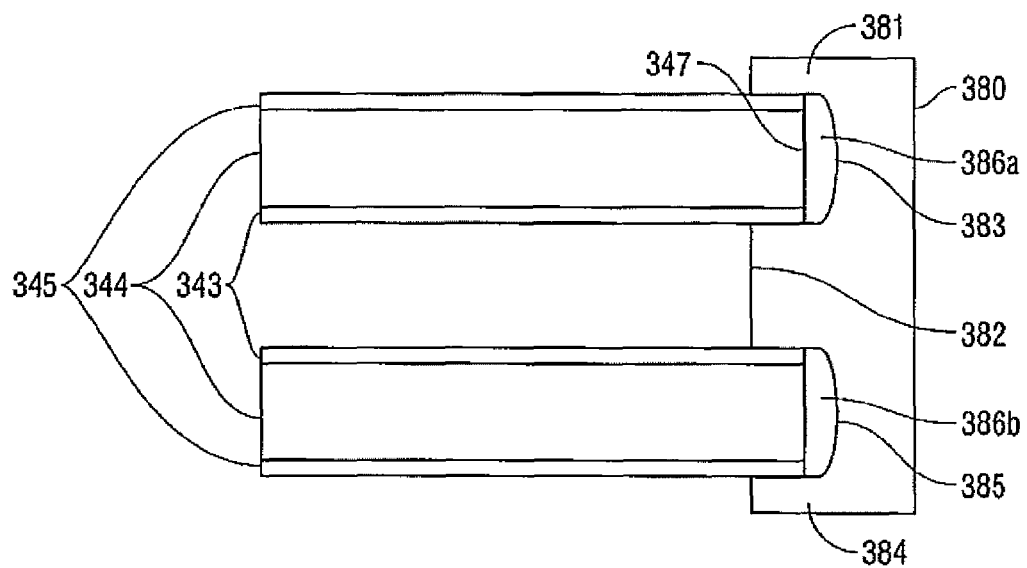
FIGS. 3A-3C show a cross-sectional view of one embodiment which describes the encapsulation of an edge of a medical device according to the present disclosure.
Figure 3B:
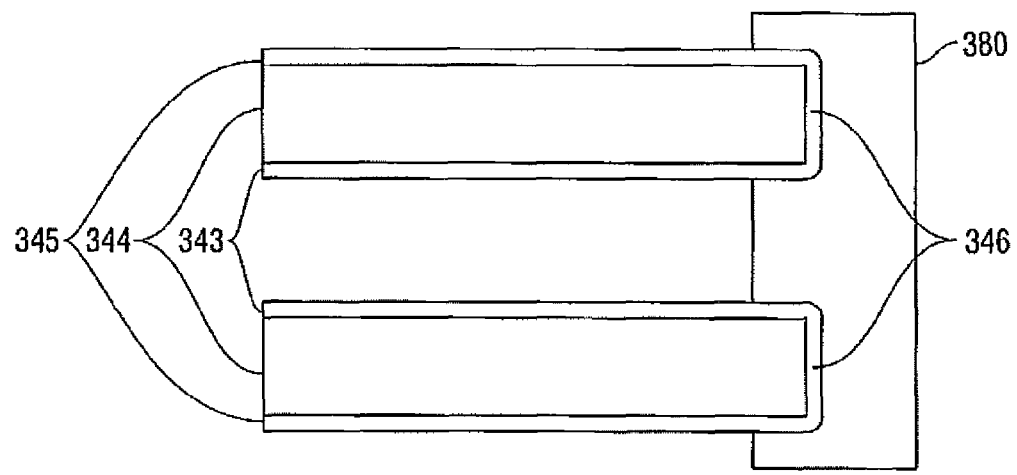
Figure 3C:
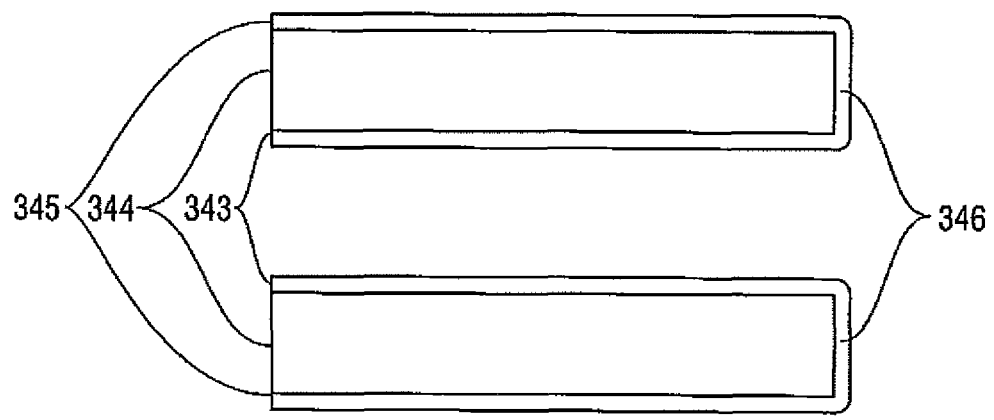

Turning now to FIGS. 3A-3C which shows a sequence wherein mold 380 is positioned along first outer edge 347 to encapsulate core layer 344 within inner layer 343 and outer layer 345. In FIG. 3A, first outer edge 347 is shown positioned within mold 380. Mold 380 includes upper flange 381 connected to middle flange 382 via upper base member 383 and lower flange 384 is connected to middle flange 382 via lower base member 385. Upper flange 381 and lower flange 384 are in contact with outer layer 345. Middle flange 382 is in contact with inner layer 343. Upper base member 383 and lower base member 385 are recessed from core layer 345 creating air gaps 386a and 386b therebetween. The mold 380 may be energized to soften the inner and outer layers 343, 345 to a flowable state. At least one of the layers flows into air gaps 386a and 386b creating an encapsulating layer 346 which encapsulates core layer 344, as shown in FIG. 3B. The encapsulating layer 346 is allowed to cure thereby encapsulating the hydrophobic core layer within a hydrophilic layer and is removed from mold 380 as shown in FIG. 3C.

Figure 4A:
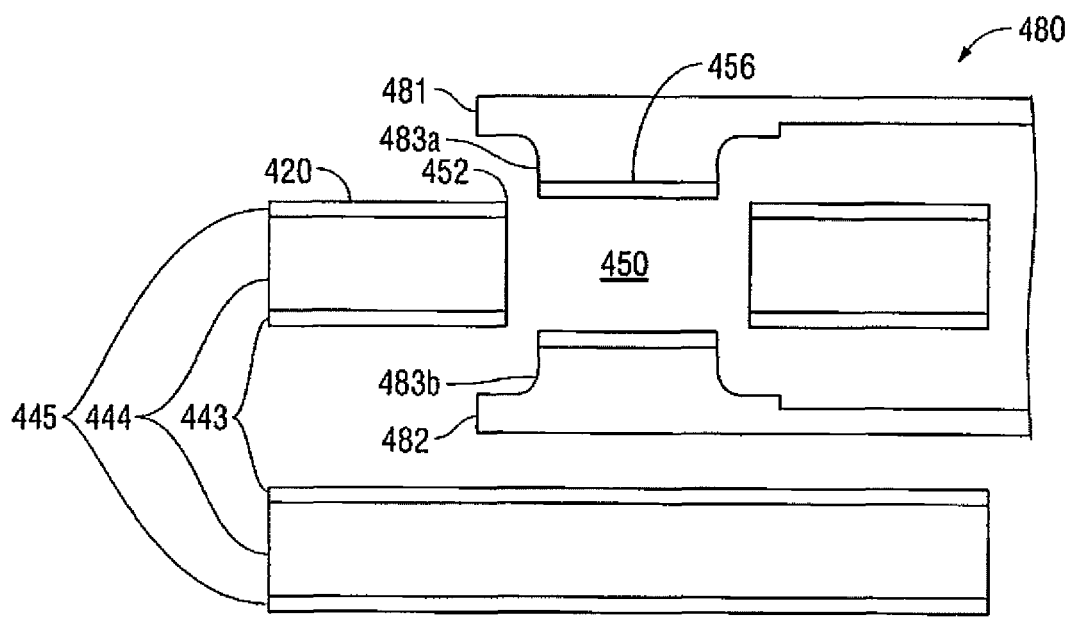
FIGS. 4A-4D show a cross-sectional view of one embodiment which describes the encapsulation of an edge of a medical device according to the present disclosure.
Figure 4B:
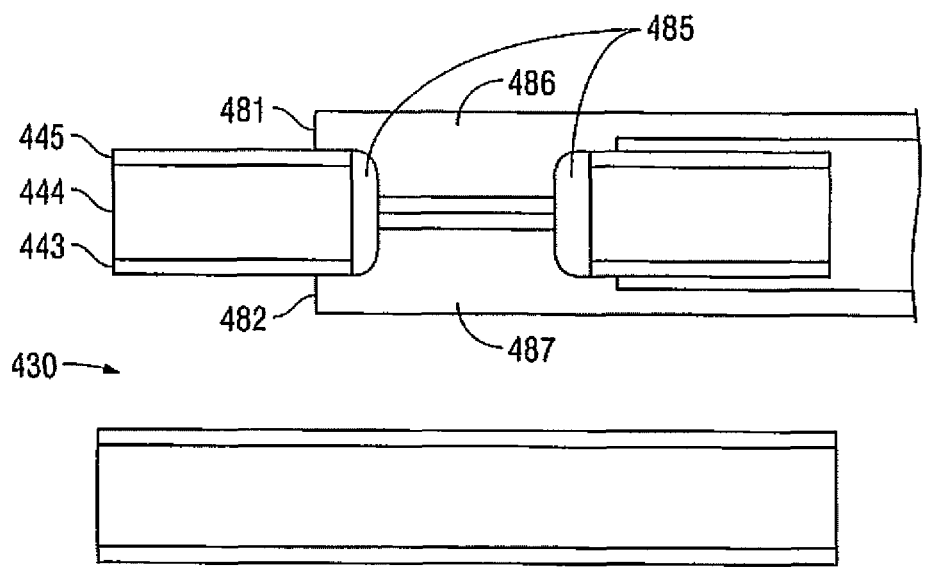
Figure 4C:
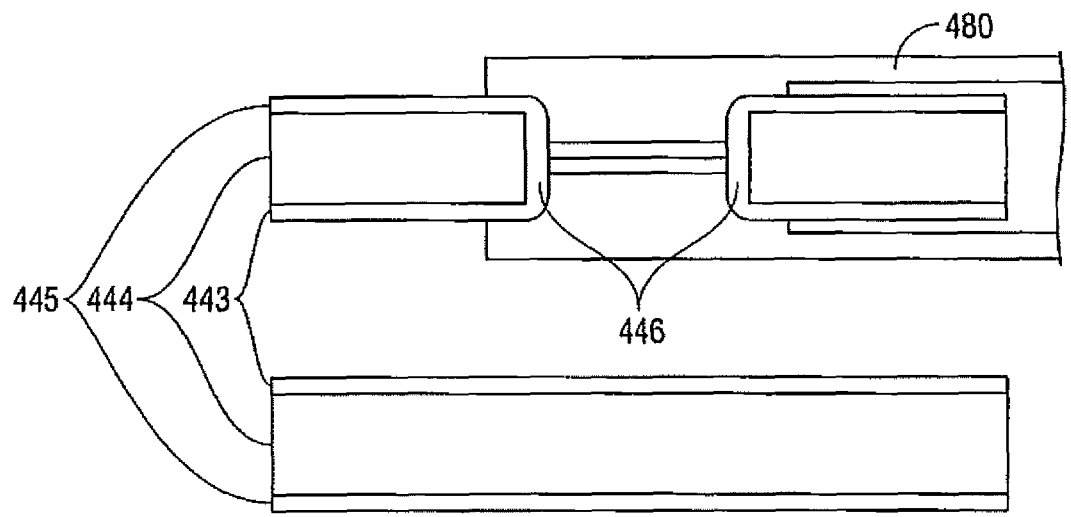
Figure 4D:
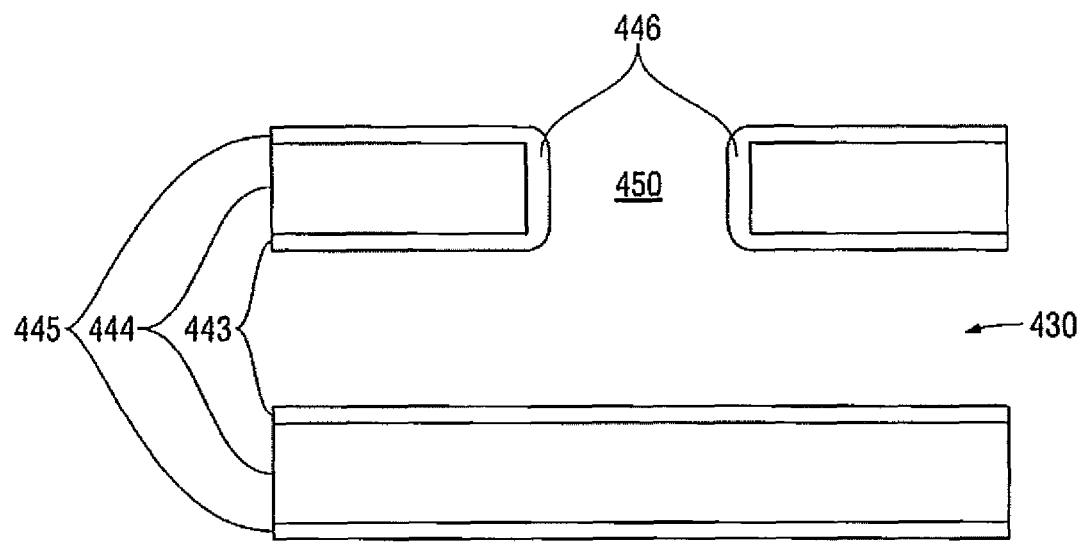

FIGS. 4A-4D also shows a sequence wherein mold 480 is positioned along inner edge 452 of hole 450 to encapsulate core layer 444 within inner layer 443 and outer layer 445. Mold 480 is shown as a two-piece tool consisting of upper member 486 and lower member 487. Upper member 486 includes upper flange 481 and upper base member 483a. Lower member 487 includes lower flange 482 and lower base member 483b. Lower member 487 is positioned within conduit 430 beneath hole 450 and upper member 486 is positioned outside wall 420 over hole 450. In FIG. 4B, upper and lower members 486, 487 are connected in hole 450 thereby forcing upper flange 481 into contact with outer layer 445 and lower flange 482 into contact with inner layer 443. Upper base member 486 and lower base member 487 are recessed from core layer 444 creating air gap 485 therebetween. Mold 480 may be energized to soften inner and outer layers 443, 445 to a flowable state. At least one of the layers may then flow into air gap 485 creating an encapsulating layer 446 which covers core layer 444, as shown in FIG. 4C. The encapsulating layer 446 is then allowed to cure and/or harden and mold 480 is withdrawn from the inner edge of the device thereby creating an inner edge of the hole wherein the hydrophobic core layer is encapsulated by the hydrophilic encapsulating layer as shown in FIG. 4D.

Although the base members of the molds shown in FIGS. 3A-3C and 4A-4D are rounded, it is envisioned that the base members may be of any shape or dimension thereby creating an encapsulated edge of any shape and dimension as well. For instance the base member of the mold may be square to create squared encapsulated edges.

It should be understood that various modifications may be made to the embodiments disclosed herein. For example, the devices described herein may include multiple conduits. As another example, the multilayer wall may include varying layers along different portions of the device. Thus, those skilled in the art will envision other modifications within the scope and spirit of the claims.

What is claimed is:

1. A method of encapsulating a core layer of a multilayer wall of a medical device comprising: providing a medical device having a body defining a conduit, the body including a multilayer wall having an outer edge along at least one of a proximal end and a distal end, wherein the multilayer wall includes a core layer positioned between an inner layer and an outer layer; positioning a mold on at least one of the proximal and distal ends of the wall contacting at least one of the inner and outer layers and creating a cavity between the mold and the end of the wall along the core layer; softening at least one of the inner and outer layers positioned within the mold to flow into the cavity and cover the core layer.

2. The method of claim 1 wherein the inner layer comprises a hydrophilic material selected from the group consisting of hydrophilic polyurethanes, sodium alginates, potassium alginates, calcium alginates, carboxymethylcellulose, gelatin, polyvinyl alcohols, collagen, pectin, chitin, chitosan, poly (.alpha.-amino acids), polycaprolactone, polyvinylpyrrolidone, polyethylene oxides, polyethers, polysaccharides, polyhydroxyacrylate, polymethacrylate, dextran, xanthan, hydroxypropyl cellulose, methyl cellulose, bioabsorbable glasses, acrylates, methacrylates and combinations thereof.

3. The method of claim 1 wherein the inner layer further comprises a bioactive agent.

4. The method of claim 1 wherein the outer layer comprises a hydrophilic material selected from the group consisting of hydrophilic polyurethanes, sodium alginates, potassium alginates, calcium alginates, carboxymethylcellulose, gelatin, polyvinyl alcohols, collagen, pectin, chitin, chitosan, poly(.alpha.-amino acids), polycaprolactone, polyvinylpyrrolidone, polyethylene oxides, polyethers, polysaccharides, polyhydroxyacrylate, polymethacrylate, dextran, xanthan, hydroxypropyl cellulose, methyl cellulose, bioabsorbable glasses, acrylates, methacrylates and combinations thereof.

5. The method of claim 1 wherein the outer layer further comprises a bioactive agent.

6. The method of claim 1 wherein the core layer comprises a hydrophobic material selected from the group consisting of polypropylene, polyethylene, hydrophobic polyurethanes, silicones, silicon rubbers, siloxanes, polydimethylsiloxanes, polyvinyl chloride and combinations thereof.

7. The method of claim 1 wherein the medical device is selected from the group consisting of tracheal tubes, nasal cannulae, stents, administration tubes, duodenal tubes, rectal tubes, drainage tubes, feeding tubes, breathing tubes, intravenous tubes, suction catheters, delivery catheters, breathing circuits, connectors, and adaptors.

8. A method of encapsulating a core layer of a multilayer wall of a medical device comprising: providing a medical device having a body defining a conduit, the body including a multilayer wall having a core layer positioned between an inner layer and an outer layer; wherein the multilayer wall further includes a hole defined therein by an inner edge; positioning a mold into the hole defined within the multilayer wall contacting at least one of the inner and outer layers and creating a cavity between the mold and the inner edge of the hole in the wall along the core layer; and softening at least one of the inner and outer layers positioned within the mold to flow into the cavity and cover the core layer.

9. The method of claim 8 wherein the inner layer comprises a hydrophilic material selected from the group consisting of hydrophilic polyurethanes, sodium alginates, potassium alginates, calcium alginates, carboxymethylcellulose, gelatin, polyvinyl alcohols, collagen, pectin, chitin, chitosan, poly(.alpha.-amino acids), polycaprolactone, polyvinylpyrrolidone, polyethylene oxides, polyethers, polysaccharides, polyhydroxyacrylate, polymethacrylate, dextran, xanthan, hydroxypropyl cellulose, methyl cellulose, bioabsorbable glasses, acrylates, methacrylates and combinations thereof.

10. The method of claim 8 wherein the inner layer further comprises a bioactive agent.

11. The method of claim 8 wherein the outer layer comprises a hydrophilic material selected from the group consisting of hydrophilic polyurethanes, sodium alginates, potassium alginates, calcium alginates, carboxymethylcellulose, gelatin, polyvinyl alcohols, collagen, pectin, chitin, chitosan, poly(.alpha.-amino acids), polycaprolactone, polyvinylpyrrolidone, polyethylene oxides, polyethers, polysaccharides, polyhydroxyacrylate, polymethacrylate, dextran, xanthan, hydroxypropyl cellulose, methyl cellulose, bioabsorbable glasses, acrylates, methacrylates and combinations thereof.

12. The method of claim 8 wherein the outer layer further comprises a bioactive agent.

13. The method of claim 8 wherein the core layer comprises a hydrophobic material selected from the group consisting of polypropylene, polyethylene, hydrophobic polyurethanes, silicones, silicon rubbers, siloxanes, polydimethylsiloxanes, polyvinyl chloride and combinations thereof.

14. The method of claim 8 wherein the medical device is selected from the group consisting of tracheal tubes, nasal cannulae, stents, administration tubes, duodenal tubes, rectal tubes, drainage tubes, feeding tubes, breathing tubes, intravenous tubes, suction catheters, delivery catheters, breathing circuits, connectors, and adaptors.

15. The method of claim 1 wherein the inner and outer layers possess a melting temperature which is lower than a melting temperature of the core layer.

16. The method of claim 15 wherein the melting temperature of the inner and outer layers is different than the melting temperature of the core layer by at least 10° C.

17. The method of claim 15 wherein the melting temperature of the inner and outer layers is different than the melting temperature of the core layer by at least 20° C.

18. The method of claim 1 wherein the inner and outer layers possess a melt flow viscosity which is lower than a melt flow viscosity of the core layer.

19. The method of claim 18 wherein the melt flow viscosity of the inner and outer layers is different than the melt flow viscosity of the core layer by at least 5 g/10 mins. at a temperature of 120° C.

20. The method of claim 1 wherein the mold includes an upper flange connected to a middle flange via an upper base member, wherein the upper flange is in contact with the outer layer, the middle flange is in contact with the inner layer, and the upper base member is recessed from the core layer creating the cavity along the core layer.

21. The method of claim 20 wherein the mold further comprises a lower flange connected to the middle flange via a lower base member, wherein the lower flange is in contact with the outer layer and the lower base member is recessed from the core layer creating the cavity along the core layer.

22. The method of claim 8 wherein the inner and outer layers possess a melting temperature which is lower than a melting temperature of the core layer.

23. The method of claim 13 wherein the melting temperature of the inner and outer layers is different than the melting temperature of the core layer by at least 10° C.

24. The method of claim 13 wherein the melting temperature of the inner and outer layers is different than the melting temperature of the core layer by at least 20° C.

25. The method of claim 8 wherein the inner and outer layers possess a melt flow viscosity which is lower than a melt flow viscosity of the core layer.

26. The method of claim 25 wherein the melt flow viscosity of the inner and outer layers is different than the melt flow viscosity of the core layer by at least 5 g/10 mins. at a temperature of 120° C.

27. The method of claim 8 wherein the mold includes an upper flange connected to an upper base member and a lower flange connected to a lower base member, wherein the upper flange is in contact with the outer layer, the lower flange is in contact with the inner layer, and the upper base member and the lower base member are recessed from the core layer creating the cavity along the core layer of the inner edge.

* * * * *